(12) United States Patent
Casey et al.

(10) Patent No.: US 8,546,445 B2
(45) Date of Patent: Oct. 1, 2013

(54) ORAL COMPOSITION

(75) Inventors: John Casey, Sharnbrook (GB); Gail Jenkins, Sharnbrook (GB); Linda Jane Wainwright, Sharnbrook (GB)

(73) Assignee: Conopco, Inc., Englewood Clifffs, NJ (US)

( * ) Notice: Subject to any disclaimer, the term of this patent is extended or adjusted under 35 U.S.C. 154(b) by 109 days.

(21) Appl. No.: 13/132,932

(22) PCT Filed: Dec. 3, 2009

(86) PCT No.: PCT/EP2009/066359
§ 371 (c)(1),
(2), (4) Date: Jun. 6, 2011

(87) PCT Pub. No.: WO2010/066641
PCT Pub. Date: Jun. 17, 2010

(65) Prior Publication Data
US 2011/0237660 A1 Sep. 29, 2011

(30) Foreign Application Priority Data
Dec. 11, 2008 (EP) .................................... 08171313

(51) Int. Cl.
*A61K 31/352* (2006.01)

(52) U.S. Cl.
USPC ....................................................... 514/456

(58) Field of Classification Search
USPC ....................................................... 514/456
See application file for complete search history.

(56) References Cited

U.S. PATENT DOCUMENTS

| | | | |
|---|---|---|---|
| 6,423,365 B1 | 7/2002 | Nair | |
| 7,501,556 B2 * | 3/2009 | Colliver et al. | 800/282 |
| 2002/0068121 A1 | 6/2002 | Green | |
| 2003/0138531 A1 | 7/2003 | Saito | |
| 2006/0078533 A1 | 4/2006 | Omoigui | |
| 2007/0116779 A1 | 5/2007 | Mazzio | |

FOREIGN PATENT DOCUMENTS

| | | |
|---|---|---|
| EP | 1629723 A1 | 1/2006 |
| EP | 1640001 A1 | 3/2006 |
| WO | WO2005092121 A2 | 10/2005 |
| WO | WO2006024545 A1 | 3/2006 |
| WO | WO2006056293 A1 | 6/2006 |
| WO | WO2008043856 A1 | 4/2008 |

OTHER PUBLICATIONS

Espinosa-Alonso, Polyphenols in Wild and Weedy Mexican Common Beans, Journal of Agricultural and Food Chem, ., vol. 54, No. 12, pp. 4436-4444, Jan. 1, 2006.
Shon, Antioxidant and free radical scavenging activity of methanol extract, Journal of Food Composition and Analysis, ., vol. 20, No. 2, pp. 113-118, Elsevier, Nov. 24, 2006.
Potter, Characteristics of wild blueberry-soy beverages, LWT, ., vol. 40, No. 5, pp. 4807-4814, Elsevier, 2007.
Wang, Cyanidin-3-O-gamma-glucoside inhibits iNOS and COX-2 expression by inducing liver X, Life Sciences, ., vol. 83, No. 5-6, pp. 176-184, Elsevier, Aug. 2008.
Wang, Inhibitory Effects of Anthocyanins and Other Phenolic Compounds, Journal of Agriculture and Food Chemistry, ., vol. 50, No. 4, pp. 850-857, American Chemical Society, Feb. 13, 2002.
Huang, In vitro and in vivo evaluation of topical delivery and potential dermal use of soy, International Journal of Pharmaceutics, ., vol. 364, No. 1, pp. 36-44, Elsevier, Nov. 1, 2008.
PCT International Search Report in PCT application PCT/EP2009/066359.
Farrar, Acne: Inflammation, Clinics in Dermatology, 2004, 380-384, 22, GB.
Holland, The Role of Inflammation in the Pathogenesis of Acne and Acne Scarring, Seminars in Cutaneous Medicine and Surgery, 2005, P79-83, 24, GB.
Jeremy et al, Inflammatory Events are Involved in Acne Lesion Initiation, The Journal of Investigative Dermatology, Jul. 1, 2003, 20-27, 121, GB.
European Search Report for Application No. 08171313 dated Feb. 19, 2009.

* cited by examiner

*Primary Examiner* — Jennifer M Kim
(74) *Attorney, Agent, or Firm* — Michael P. Aronson

(57) ABSTRACT

A composition which is adapted for oral consumption comprising daidzein and an anthocyanidin, wherein the weight ratio of daidzein to anthocyanidin is in the range of from 1:1 to 1:100, wherein the daidzein is in the form of a pre-prepared aqueous dispersion, and wherein the composition is free of soy protein, which can exhibit an anti-inflammatory effect in skin, the use of a composition containing daidzein and an anthocyanidin for obtaining an anti-inflammatory effect in the skin and a method of reducing skin inflammation through the oral consumption of the composition.

6 Claims, 3 Drawing Sheets

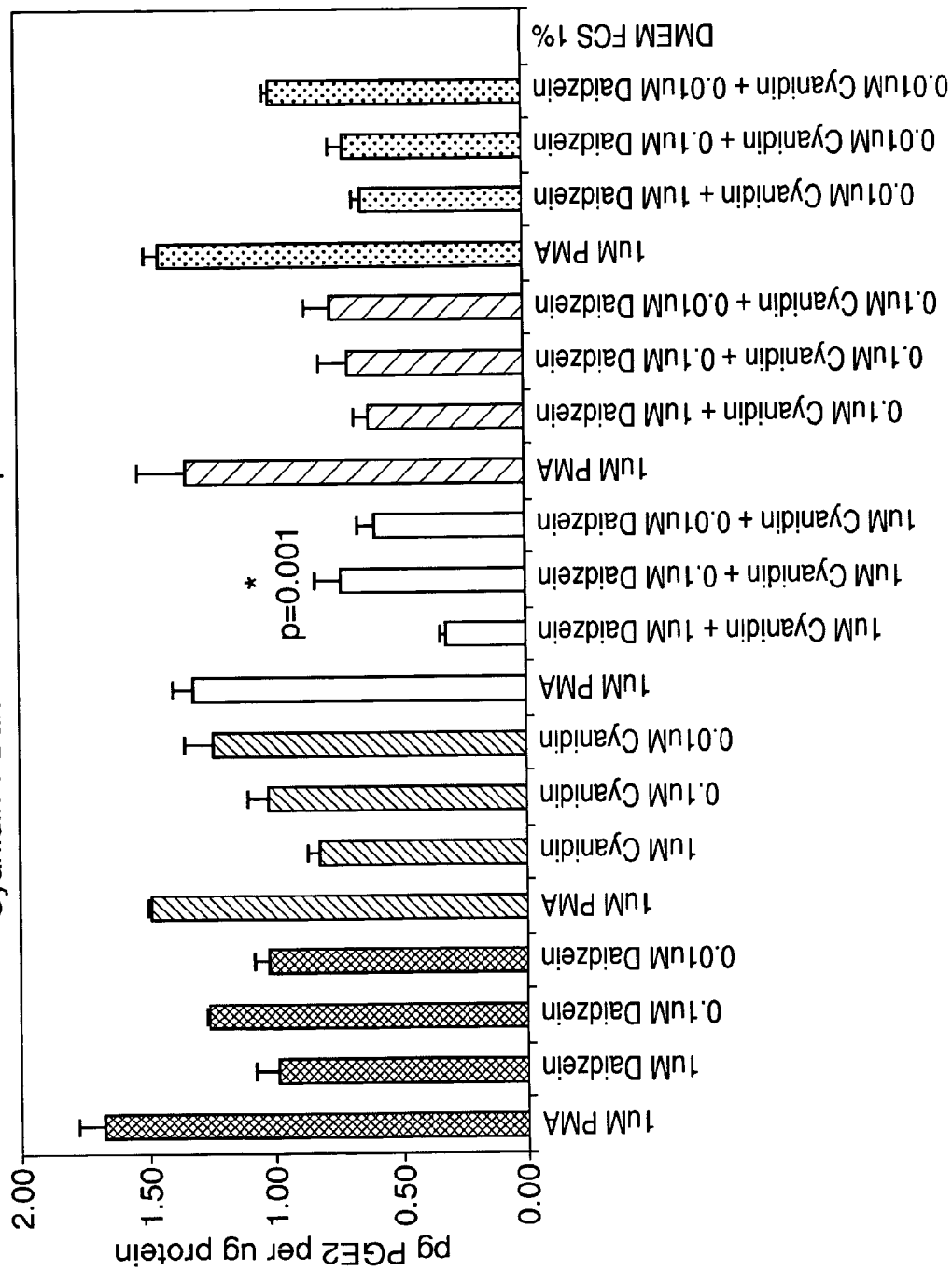

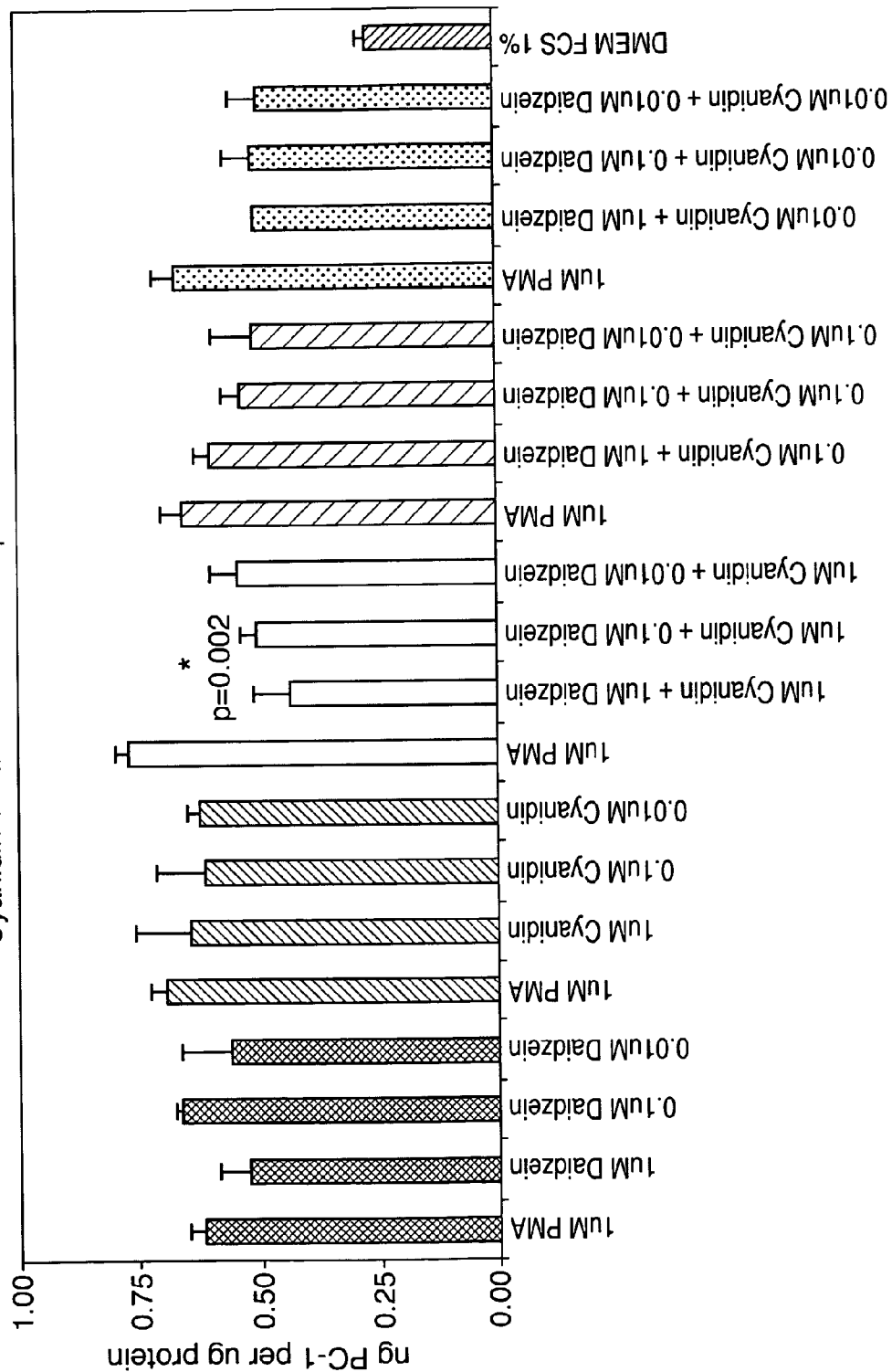

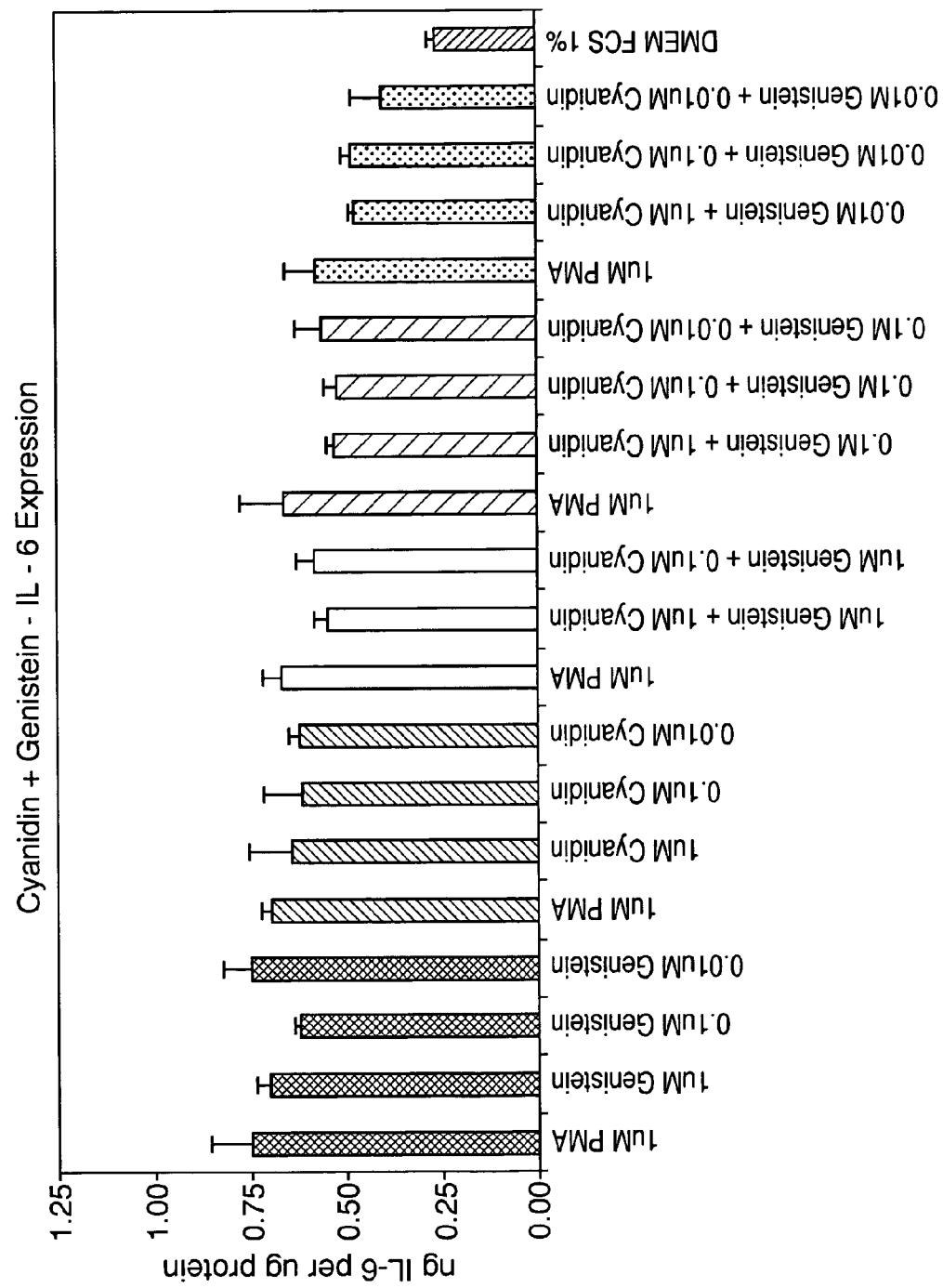

ORAL COMPOSITION

The present invention relates to a composition for oral consumption which, when taken orally, can have benefits for the skin and to the use of a combination of active compounds.

Improving the appearance and feel of human skin has received a great deal of research effort. However, the vast majority of commercially available products address this problem by acting on the exterior of the skin. The most common form of these is a topical skin cream. However such topical applications have their limitations and deal primarily with the dead surface layers of the skin. It is known that certain ingredients can provide improvements in skin appearance and texture from being ingested. Such ingredients thus act from the interior of the skin and therefore can provide greater opportunities for improving the skin by accessing the living interior. Furthermore such an effect may be perceived by the general public as being more potent or medical in nature than a topical application.

Our co-pending international application number PCT/EP2005/011658 relates to stable consumable emulsions.

EP 1 640 001 relates to a therapeutic mixture for oral use including a vitamin, a soy derivative and a polyphenol. The mixture may be used to treat cardiovascular diseases.

US 2003/0138531 relates to a powdered composition for food and drink which includes soy protein isolate and an anthocyanin. The soy protein is present in from 50 to 95% by weight of the powdered mixture and the anthocyanin component in 4 to 49% by weight. The powders are intended primarily for dissolution or suspension in a liquid to form a fruit flavoured drink.

U.S. Pat. No. 6,423,365 describes a method of preparation of cherry derived compositions which may be used as food additives or dietary supplements. The compositions contain anthocyanins, bioflavinoids and phenolics, including daidzein.

EP 1 629 723 describes a functional food comprising soy flour and lignan containing rye bran, supplemented by flavour-contributing components such as dried lingonberries or bilberries.

Formulations containing wild blueberry ingredients with soy protein are disclosed in Potter et al (LWT 40, 807-814 (2007).

US 2006/0078533 A1 discloses a method for the prevention and treatment of aging and age-related disorders based on inhibition of Interleukin-6 inflammation through regulation of cholesterol metabolism, isoprenoid depletion and/or inhibition of the signal transduction pathway.

US 2007/0116779 A1 discloses a neutraceutical designed to antagonize major mitigating factors specific to the degenerative process that occurs in Parkinson's disease.

WO 2006/024545 A1 discloses the use of at least two compounds of which the first compound is a natural compound of a specific general formula which are identified as PARP-1 inhibitors and a second compound which is a NAD+ precursor for preparing medicaments, medical foods or nutraceuticals.

WO 2005/092121 A2 discloses a composition comprising all essential nutrients of a fruit or a plant material which has increased stability, bioavailability and miscibility, and the process of forming the same.

US 2002/0068121 A1 discloses that blends of quercetin and isoflavones from the group consisting of genistein, daidzein and glycetin display synergistic effects when applied as anti-inflammatory agents or as skin agents in particular for anti-aging purposes.

The feasibility of skin adsorption of soy isoflavones was evaluated in Huang et al (International J. of Pharmaceutics, 364, 36-44 (2008)).

Wang et al (Life Sciences, 83, 176-184 (2008)) discloses that pre-treatment of THP-1 macrophages with cyanidin-3-0-β-glucoside for 12 hours can enhance the expression and transcriptional activities of the nuclear receptor peroxisome proliferators-activated receptor and liver X receptor α.

There remains a need for orally administered compositions that have improved properties for imparting benefits to the skin of the consumer.

SUMMARY OF THE INVENTION

In a first aspect, the invention provides a composition which is adapted for oral consumption comprising daidzein and an anthocyanidin, wherein the weight ratio of daidzein to anthocyanidin is in the range of from 1:1 to 1:100, wherein the daidzein is in the form of a pre-prepared aqueous dispersion, and wherein the composition is free of soy protein. This composition may provide an anti-inflammatory effect in skin.

It has been observed that if the daidzein is not in the form of a pre-prepared aqueous dispersion, there may be a tendency for the daidzein to sediment or clump, which would prevent absorption of daidzein in the gut. In turn, this would adversely affect the beneficial effects observed as demonstrated in the examples.

The inventive composition is an oral composition i.e. it is adapted for oral consumption. As such, the composition is edible and non-toxic.

In a second aspect, the invention provides use of daidzein and cyanidin in the manufacture of a composition, which is adapted for oral consumption, for obtaining an anti-inflammatory effect in skin. In another embodiment of the second aspect, a composition is provided, the composition comprising daidzein and cyanidin for use in obtaining an anti-inflammatory effect in skin.

In a third aspect of the invention, use is provided of daidzein and cyanidin in the manufacture of a composition, which is adapted for oral consumption, for treating acne. In another embodiment of the third aspect, a composition is provided, the composition comprising daidzein and cyanidin for treating acne.

In a fourth aspect of the invention a method is provided of reducing inflammation in skin which comprises providing a subject in need thereof with the inventive composition.

In a fifth aspect of the invention, a method of treating acne is provided which comprises providing a subject in need thereof with the inventive composition.

In the second to fifth aspects of the invention the daily dosage level of daidzein is up to 100 mg, preferably from 1 to 100 mg, most preferably from 10 to 50 mg and the daily dosage level of anthocyanidin is up to 1000 mg, preferably from 10 to 1000 mg, most preferably from 50 to 750 mg.

In a sixth aspect of the invention, a method of manufacturing a composition according to the first aspect is provided, the method comprising the steps of:

(a) preparing a dispersion of daidzein in water at 40-95, preferably 50-85° C. and leaving to stand for at least 5, preferably at least 10, most preferably at least 15 minutes thereby to produce a pre-prepared aqueous dispersion of daidzein; and then (b) adding cyanidin and any other water-soluble ingredients to the pre-prepared aqueous dispersion of daidzein thereby to produce an aqueous phase;

(c) optionally dissolving any oil-soluble ingredients in an oil thereby to produce an oil phase;

(d) optionally blending the aqueous phase and oil phase thereby to produce an emulsion;

wherein step (c) may precede step (a).

The invention is based on the surprising finding of a synergistic effect between daidzein and an anthocyanin.

The composition of the invention thus comprises daidzein and an anthocyanidin in the range of 1:1 to 1:100, more typically in the range 1:1 to 1:50, often 1:1 to 1:20, conveniently 1:1 to 1:15, preferably 1:1 to 1:10.

Preferably the inventive composition is in the form of a substantially homogeneous aqueous emulsion, suspension or dispersion.

Suitable anthocyanidins include compounds such as aurantindin, cyanin, cyanidin, delphinidin, europindin, luteolindin, pelargonidin, malvidin, peonidin, petunidin, idaein, keracyanin, asterin and rosindin. A particularly preferred anthocyanidin is cyanidin, a natural organic compound which is classified as a flavonoid.

Unless otherwise stated, the term "anthocyanidin" is intended to include not only the anthocyanidin compound itself, but also related anthocyanin derivatives such as glucoside, rutinoside and sophoroside.

Accordingly the composition of the invention may include as the "anthocyanidin" component one or more of cyanidin, cyanin, idaein, keracyanin, asterin and derivatives thereof either alone or in combination. Typically cyanidin itself will be present either alone or in combination with one or more other anthocyanidin type compounds. Often when cyanidin is present, the compounds cyanin, idaein, keracyanin, asterin and their derivatives are present in trace amounts only as would be common for natural plant extracts of a substance. For instance, the related compounds may be present in less than 1%, preferably less than 0.2%, often less than 0.05%, more often less than 0.01% by weight of the cyanidin component of the composition. It is preferred that where cyanidin is present in combination with other anthocyanidin compounds, that the cyanidin will be present as more than 50%, preferably more than 75% by weight of the anthocyanidin component.

The composition of the invention preferably comprises anthocyanidin in an amount of from 0.0001 to 0.1%, more preferably from 0.001 to 0.05%, even more preferably from 0.005 to 0.04%, most preferably from 0.005 to 0.025%, such as from 0.01 to 0.025% by weight. Often the concentration of cyanidin will be in the range 0.001 to 5 µM, preferably 0.01 to 1.5 µM, more preferably 0.5 to 1.2 µM, most preferably 0.8 to 1.2 µM.

Anthocyanidins including cyanidin are pigments found in many red berries including but not limited to bilberry, blackberry, blueberry, cherry, cranberry, elderberry, hawthorn, loganberry, acai berry and raspberry. They can also be found in other fruits such as apples and plums. The highest concentrations of anthocyanidins are found in the skin of the fruit.

Daidzein is an isoflavone found in soy and red clover. Unless otherwise stated, the term "daidzein" is intended to include not only daidzein but also metabolites such as o-desmethylangolensin and dihydrodaidzein and derivatives thereof either alone or in combination. Typically daidzein itself will be present either alone or in combination with one or more derivatives or metabolites. Often when daidzein is present, the metabolites or derivatives are present in trace amounts only as would be common for natural plant extracts of a substance. For instance the derivatives may be present in less than 1%, preferably less than 0.2%, often less than 0.05%, more often less than 0.01% by weight of the daidzein component of the composition. It is preferred that, where daidzein is present in combination with daidzein derivatives or metabolites, the daidzein will be present as more than 50%, preferably 75% by weight of the daidzein component of the composition.

The composition of the invention preferably comprises daidzein in an amount of from 0.0001 to 0.1%, more preferably from 0.001 to 0.05%, even more preferably from 0.005 to 0.04%, most preferably from 0.005 to 0.025%, such as from 0.01 to 0.025% by weight of the composition. Often the concentration of daidzein in the composition will be in the range 0.001 to 5 µM, preferably 0.01 to 1.5 µM, more preferably 0.5 to 1.2 µM, most preferably 0.8 to 1.2 µM.

Preferably, the daidzein is present as a component of a natural product or an extract or concentrate thereof. The natural product is preferably soy or red clover, more preferably soy. The daidzein, when it is from soy, is preferably purified at least to some extent by removal of soy protein. Therefore compositions of the invention preferably contain less than 1%, more preferably less than 0.5%, even more preferably less than 0.1%, such as less than 0.01% or less than 0.001% or less than 0.0001% by weight of soy protein.

The composition preferably comprises one or more further components selected from the group consisting of antioxidants, flavouring agents, preservatives and stabilisers.

The composition of the invention may take any suitable form, including, for example food products and nutritional supplements. Compositions for oral consumption include beverages, bars and other liquid and solid forms such as tablets, pills, capsules and powders (which may contain crystalline material), as well as spreads, margarines, creams, sauces, dressings, mayonnaises, ice creams, fillings, confectionaries and cereals.

In one embodiment of the invention, the composition is edible and is preferably water based, i.e. comprises at least 50% by weight water, preferably at least 60% by weight or even at least 70% by weight water. The water may be added or may be derived from a natural product that contains the daidzein and/or the anthocyanin. It may be either liquid or frozen. The product thus has the sensation of being a regular water-based product and can be consumed on a regular basis as part of a consumer's normal diet. For example it could replace a fruit juice normally consumed at breakfast time. The composition of the invention is preferably packaged as a beverage, for example, in a container such as a carton or a bottle of coated paper or cardboard, glass or plastic. The container preferably has a volume of from 10 to 500 ml, such as from 20 to 100 ml.

In an alternative embodiment, the composition of the invention is contained in a capsule, provided together with instructions informing the user of a proposed dosage regime. Typically the daidzein and/or the anthocyanin will then be in a more concentrated form. The capsule may be made of any suitable material well known in the art such as gelatin. The capsule is adapted to be swallowed by the consumer and typically one or two capsules will be taken from one to four times per day. Each capsule preferably comprises from 0.1 to 1000 mg of daidzein, typically from 5 to 100 mg, often from 20 to 50 mg. The anthocyanin is typically present in the range 0.1 to 1000 mg, alternatively 5 to 100 mg and preferably 20 to 50 mg.

Alternatively the composition of the invention may be included as one component of a complex food product, for instance the composition may be present in solid or gelatinous form as a filling or layer within a bar or similar product. The composition may therefore be included in a wide range of everyday food stuffs, for instance in "health food" bars which could be eaten as an alternative to other snack foods.

One or more additional antioxidants are preferably present in the compositions of the invention in order to prevent or slow down the natural oxidative degradation of the composition. Suitable additional antioxidants can be selected, although not exclusively, from the following list, either singularly or in combination: TBHQ, ascorbyl esters (e.g. ascorbyl palmitate), ascorbic acid, tocopherols, rosemary extract, fruit concentrates or extracts, black or green tea extract, propyl gallate, butylated hydroxyanisole (BHA), butylated hydroxytoluene (BHT), citric acid or esters, tocotrienols, polyphenols, phenolic compounds, flavonoids and oxygen scavengers. Especially preferred additional antioxidants are vitamins C and E. Not only are these effective antioxidants but they also have been shown to give skin benefits when consumed. The amount of additional antioxidant may be added sufficient to prevent the composition from going rancid over a typical shelf-life of at least 6 months. Clearly the amount of antioxidant will depend on the type and activity of the antioxidant used.

The compositions of the invention may comprise a flavouring, although the addition of a flavouring may be unnecessary if the daidzein or anthocyanidin is provided by a flavoured substance such as a fruit juice. Suitable flavouring agents may be natural or synthetic. Flavouring agents may be required to make the product more palatable for consumption.

The compositions may comprise an emulsifier, more preferably a food grade phospholipid emulsifier. It is preferred that the phospholipid emulsifier is lecithin. Phospholipid emulsifiers are oil soluble, but the lecithin can be added to either phase prior to emulsification. Preferably it is added to the aqueous phase. Any emulsifier is preferably present in the composition in an amount of at least 0.01%, preferably from 0.05 to 3%, more preferably from 0.1 to 1% by weight.

The composition of the invention may comprise polyunsaturated fatty acids, such as an omega-3 fatty acid (i.e. an unsaturated carboxylic acid having from 12 to 26 carbon atoms). Preferred omega-3 fatty acids are those selected from docosahexaenoic acid (DHA), eicosapentaenoic acid (EPA) and mixtures thereof. Suitable polyunsaturated fatty acids may also be selected from oleic acid, linoleic acid, γ-linoleic acid, linolenic acid, arachidonic acid. The polyunsaturated fatty acid may be present as a component of a natural oil, such as a fish oil.

The composition may also comprise carotenoids, such as in an amount of from 0.0005 to 0.1%, for example from 0.002 to 0.04% by weight. The carotenoids, being oil soluble, would be comprised predominantly within the oil phase. Highly preferred carotenoids are β-carotene, and lycopene. These carotenoids provide moderate protection from ultra-violet induced erythema, thought to be due to their antioxidant functionality including scavenging of reactive oxygen species.

The composition may also comprise additional soy isoflavones (including genistein in glycosylated and/or non-glycosylated form), typically in an amount of from 0.0001 to 0.1% by weight.

The composition of the present invention may be made by preparing an aqueous phase and an oil phase. Firstly an aqueous dispersion of daidzein is prepared at 75 degrees Celsius and left to stand for about 15 minutes and then the remaining water-soluble ingredients are added to the pre-prepared dispersion and the oil-soluble ingredients are put in the oil phase. If an emulsifier is used, it is preferred that it is added to the aqueous phase. The oil phase and aqueous phase are then blended together to form an emulsion. In a preferred process, the oil is on a powdered carrier material to assist emulsion formation. The emulsion may then be packaged in a sealed container such as a metal, coated cardboard (e.g. Tetra Pak) or plastics container. The container is then preferably sealed so as to give no headspace or a gas-filled (e.g. nitrogen or carbon dioxide) headspace. This assists still further in preventing oxidation. Alternatively the emulsion may be frozen and packaged and sold as a frozen consumer product.

Oil used in the sixth aspect of the invention may be selected from palm oil, cocoa butter, coconut oil, palm kernel oil, soy bean oil, olive oil, sunflower oil, rape seed oil, safflower oil, corn oil, cotton seed oil, cocoa butter equivalents, cocoa butter replacers, fish oil, borage oil, pine nut oil, coriander oil, fungal oils, fractions thereof, hardened varieties thereof, fractions of the hardened varieties and mixtures thereof.

Benefits of the anti-inflammatory effects in skin may include one or more of: anti-ageing effects: reduced dryness; increased firmness; increased elasticity; reduced fine lines and wrinkles; fewer spots, pimples and blemishes (including acne); clearer skin; less sensitive skin; and generally healthier skin. The skin may include the skin of the whole body, preferably of the face, neck and/or hands. The skin may also include scalp skin with benefits for hair (including reduced ageing) and scalp itch or irritation. The inventive composition is preferably used for its anti-ageing and/or anti-wrinkle effects. The skin of the consumer may be described as calm and/or clear and/or blemish-free.

The following non-limiting examples illustrate the invention and do not limit its scope in any way. In the examples and throughout this specification, all percentages, parts and ratios are by weight unless indicated otherwise. Further, all percentages, weights and ratios are to be taken as modified by the term "about" unless otherwise specified. For the avoidance of doubt, all components of the inventive composition described herein may be used in any combination unless otherwise stated.

BRIEF DESCRIPTION OF THE FIGURES

The invention is now illustrated with reference to the figures which show in:

FIG. 1 the pg PGE2 per μg protein for the combination of cyanidin and daidzein in a composition;

FIG. 2 the ng IL6 per μg protein for the combination of cyanidin and daidzein in a composition; and FIG. 3 the ng IL6 per μg protein for the combination of cyanidin and genistein in a composition.

EXAMPLE

Anti-Inflammatory Synergistic Effect between a Soy Isoflavone (Daidzein) and Anthocyanin (Cyanidin) in Human Primary Dermal Fibroblasts Cell Preparation An in vitro model was developed to investigate the impact of oxidative stress on the inflammatory status of skin-derived primary dermal fibroblast cells (using PGE2 and IL6 as key markers of inflammation of the skin). The cells were prepared in the following manner:

a. Cells are grown in 6-well (9.5 cm$^2$) plates;
b. Test solutions were prepared in Dulbecco's Modified Eagle Medium (DMEM);
c. The cells were oxidatively stressed with 1 μM phorbol myristate Acetate (PMA);
d. Tissue culture supernatant and cell pellets were harvested at 24 hours (t24) post-PMA treatment; and e. All tissue culture supernatant was assayed for lactate dehydrogenase (LDH), as a measure of cytotoxicity (see below), PGE2 and IL6 synthesis.

Cytotoxicity Assay (Promega)

All tissue culture supernatant was examined for cytotoxicity using the Promega CytoTox 96 non-radioactive cytotoxicity assay. This assay quantitatively measures LDH released upon cell lysis and is a good indication of cell viability. 50 μL of tissue culture supernatant or control medium was added to duplicate wells of a 96-well microtitre plate. 50 μL of CytoTox reagent was added to each well and mixed thoroughly. The plate was incubated in the dark at room temperature for 30 minutes after which 50 μL of stop solution was added to each well and the plate read at 492 nm. Any test sample giving an absorbance value of more than double that of the control medium was considered cytotoxic. No results have been included from samples that showed any signs of cytotoxicity.

IL6 ELISA (R&D Systems)

The IL6 protein concentration of each tissue culture supernatant was assayed using the QuantGlo Q6000 Human IL6 assay (R&D Systems) according to the manufacturer's instructions.

Six IL6 standards were prepared in calibrator diluent at concentrations ranging from 0 to 3000 pg/ml. 50 μL of assay diluent and 150 μL of tissue culture supernatant or standard was added to duplicate wells. The plate was incubated at room temperature for two hours on a horizontal orbital plate shaker before being washed four times with wash buffer. 200 μL of IL6 conjugate was added to each well and the plate incubated on a horizontal orbital shaker for three hours. The plate was washed as before. Each well received 200 μL of substrate solution and the plate incubated at room temperature on the bench top for 40 minutes. The relative light unit (RLU) of each well was determined using a luminometer set with a one minute lag time, 1 second/well read time, summation mode and automatic gain on.

A standard curve was plotted of mean RLU versus IL6 concentration and the line of best fit calculated by regression analysis. The unknown concentration of IL6 protein in all the samples was estimated from this.

PGE2 High Sensitivity ELISA (R&D Systems)

The PGE2 protein concentration of each tissue culture supernatant was assayed using the DE2100 Human PGE2 assay (R&D Systems) according to the manufacturer's instructions.

Eight PGE2 standards were prepared in calibrator diluent at concentrations ranging from 0 to 1000 pg/ml. 150 μL of assay diluent and 50 μL of tissue culture supernatant or standard was added to duplicate wells. 50 μL of PGE2 HS antibody solution was added to each well and the plate incubated for 18-24 hours at 2-8° C. The plate was then washed four times with wash buffer. 200 μL of p-nitro phenyl phosphate (pNPP) substrate was added to each well and the plate incubated at room temperature for one hour. 50 μL of stop solution was then added to each well. The optical density of each well was determined using a microplate reader set to 405 nm with wavelength correction set to between 570 nm and 590 nm.

A standard curve was plotted of mean optical density versus PGE2 concentration and the line of best fit calculated by regression analysis. The unknown concentration of PGE2 protein in all the samples was estimated from this.

Materials

Genistein and daidzein were obtained from Sigma Aldrich and cyaniding purchased from Chromadex.

Results

The results are illustrated in the figures which show in:

FIG. 1 the synergistic anti-inflammatory effect (PGE2) of combining cyanidin and daidzein in a composition;

FIG. 2 the synergistic anti-inflammatory effect (IL6) of combining cyanidin and daidzein in a composition; and FIG. 3 the non-synergistic anti-inflammatory effect (IL6) of combining cyanidin and genistein in a composition.

The invention claimed is:

1. A method of reducing inflammation in skin which comprises providing a subject in need thereof with a composition which is adapted for oral consumption comprising a combination of daidzein and cyanidin which, when tested in vitro, is synergistic in reducing the expression of the inflammation markers PGE2 and IL-6; wherein the weight ratio of daidzein to cyanidin is in the range of from 1:1 to 1:100, and wherein the daidzein is in the form of a pre-prepared aqueous dispersion.

2. A method of treating acne which comprises providing a subject in need thereof with a composition which is adapted for oral consumption comprising a combination of daidzein and cyanidin which, when tested in-vitro, is synergistic in reducing the expression of the inflammation markers PGE2 and IL-6; wherein the weight ratio of daidzein to cyanidin is in the range of from 1:1 to 1:100, wherein the daidzein is in the form of a pre-prepared aqueous dispersion.

3. The method according to claim 1 wherein the weight ratio of daidzein to cyanidin is in the range of from 1:1 to 1:10.

4. The method according to claim 2, wherein the weight ratio of daizein to cyanidin is in the range of from 1:1 to 1:10.

5. The method according to claim 1, wherein the composition is free of soy protein.

6. The method according to claim 2, wherein the composition is free of soy protein.

* * * * *